United States Patent
Garel

(10) Patent No.: US 6,845,677 B2
(45) Date of Patent: Jan. 25, 2005

(54) DEVICE FOR TAKING SAMPLES FROM A MATERIAL OF GRANULAR OR POWDERY COMPOSITION

(75) Inventor: Bertrand Garel, La Membrolle sur Choisille (FR)

(73) Assignee: Agro-Systemes S.A., Membrolle sur Choisille (FR)

( * ) Notice: Subject to any disclaimer, the term of this patent is extended or adjusted under 35 U.S.C. 154(b) by 129 days.

(21) Appl. No.: 10/048,415

(22) PCT Filed: May 31, 2001

(86) PCT No.: PCT/FR01/01696

§ 371 (c)(1),
(2), (4) Date: Apr. 15, 2002

(87) PCT Pub. No.: WO01/92847

PCT Pub. Date: Dec. 6, 2001

(65) Prior Publication Data

US 2002/0148306 A1 Oct. 17, 2002

(30) Foreign Application Priority Data

May 31, 2000 (FR) .............................................. 00 07021

(51) Int. Cl.[7] .............................. G01N 1/08; E21B 49/02
(52) U.S. Cl. ................................. 73/864.43; 73/864.45; 175/20
(58) Field of Search ........................ 73/864.43–864.45, 73/864.41; 175/20

(56) References Cited

U.S. PATENT DOCUMENTS

| | | | | |
|---|---|---|---|---|
| 2,084,686 A | * | 6/1937 | Howard | 73/864.45 X |
| 2,643,858 A | * | 6/1953 | Hardman | 73/864.45 X |
| 2,868,019 A | * | 1/1959 | Bull | 73/864.45 X |
| 4,530,236 A | * | 7/1985 | van den Berg | 73/864.45 X |
| 5,408,893 A | | 4/1995 | McLeroy | 73/864.44 |

FOREIGN PATENT DOCUMENTS

| | | | | |
|---|---|---|---|---|
| CA | 1 255 514 | 6/1989 | | G01N/1/04 |
| DE | 79 25 902 | 1/1980 | | G01N/1/08 |
| DE | 42 00 426 A1 | 7/1993 | | G01N/1/04 |
| DE | 3707589 A1 | 9/1998 | | G01N/1/08 |
| DE | 197 11 305 A1 | 9/1998 | | G01N/1/04 |
| FR | 2 702 563 A1 | 9/1994 | | G01N/1/04 |
| GB | 532371 | 1/1941 | | |
| GB | 1077122 | 7/1967 | | G01N/1/12 |

* cited by examiner

Primary Examiner—Thomas P. Noland
(74) Attorney, Agent, or Firm—Nixon & Vanderhye

(57) ABSTRACT

The device for sampling material of granular or powdery composition includes a stem at one end of which a wheel is mounted intended to cause the device to rotate. At the opposite end is a driving head. The head is mounted symmetrically on the stem and includes lower and side parts of a streamlined shape. The stem has a predetermined shape to scrape material nover the entire driving depth of the device in the material to be sampled. The head has a cross section that is smaller than, equal to, or greater than the cross section of the stem and in proportions determined in relation to the nature or moisture content of the material to be sampled.

20 Claims, 3 Drawing Sheets

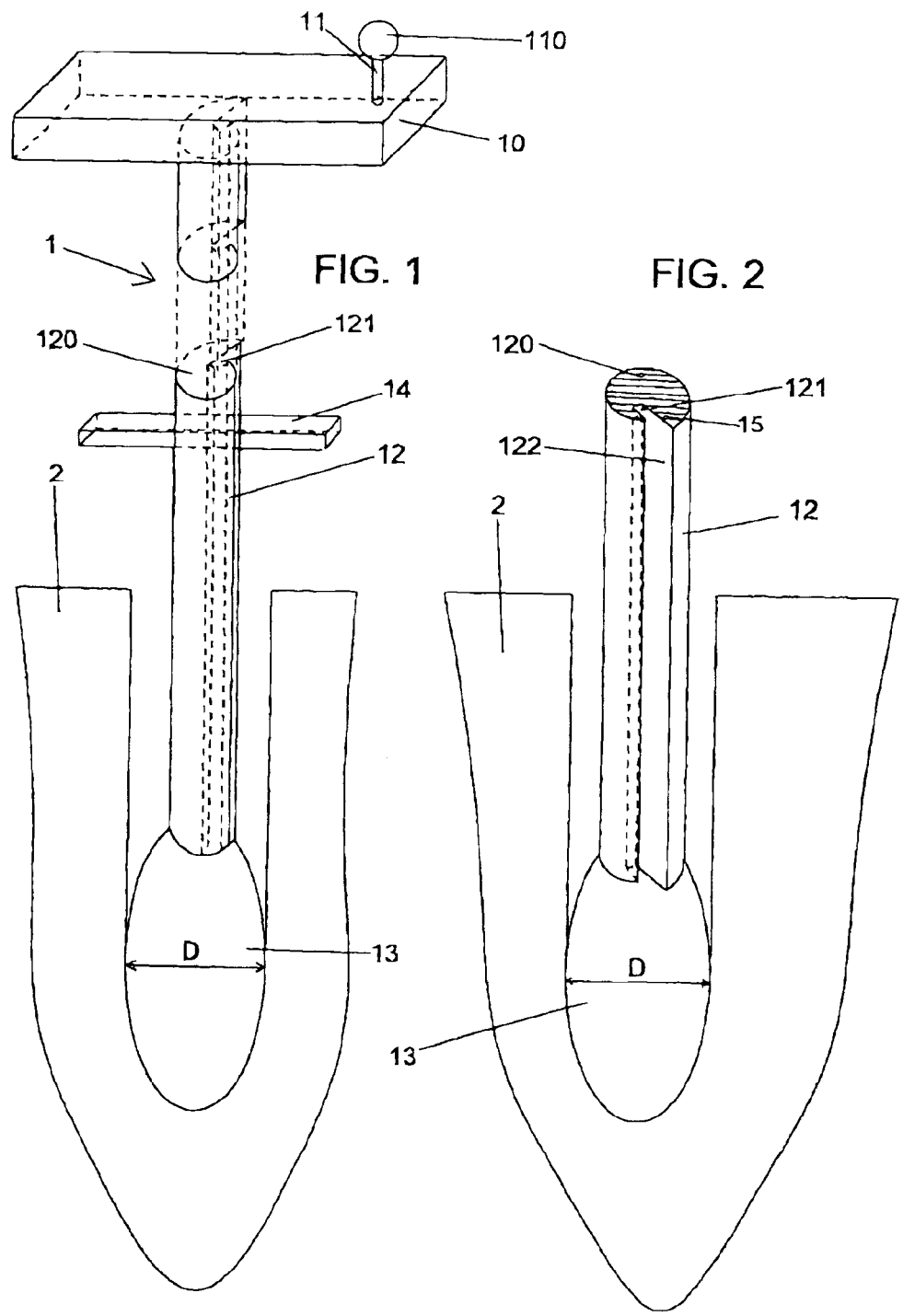

DEVICE FOR TAKING SAMPLES FROM A MATERIAL OF GRANULAR OR POWDERY COMPOSITION

FIELD OF THE INVENTION

The present invention concerns a device for sampling material of granular or powdery composition. The invention relates more particularly to an auger for taking samples in moist ground or core samples.

BACKGROUND OF THE INVENTION

Different types of auger are known in the prior art. As a general rule, the study of ground composition is made in the following manner. In a field, 10 samples are taken around a circle having a radius of 10 meters. Generally samples are taken at different depths depending upon the substances it is desired to detect. For example, to study the nitrate composition of soil, it is necessary to reach depths of approximately 90 cm. The study of nitrate composition is preferably made between October and March, at the time of year when the ground is wettest, and it is therefore easier to reach depths of 90 cm. For other soil components, the samples to be taken by the user may require lower depths, for example 30 or 60 cm.

A type of auger exists, formed of an elongated metal stem surmounted by a wheel intended to turn the stem so as to drive it downwards, which ends in a device in the shape of a gimlet intended to bore down to the desired depth and used to collect the sample at this depth by rotation. The problem with this auger lies in the fact that the same device, namely the gimlet, is used both for boring and for collecting the sample. It is therefore obvious that the soil cleared while the gimlet is driven downwards will be mixed with the soil taken at the desired depth.

In addition, if it is desired to take samples at different depths, the auger needs to be driven down to a first depth and then lifted back to the surface with the samples taken at this depth, and it is subsequently re-lowered down to a new depth, and again lifted back to the surface with the new sample taken at this second depth. This is a lengthy, tiresome process.

Finally, it often proves difficult to drive the auger down to 90 cm and to lift it back owing to the friction exerted on the gimlet and on the stem as the tool bores downwards.

Another type of auger is disclosed in document DE 3707589. This auger comprises a driving head formed of a tip fixed to the end of the stem. The head comprises a part offset towards the outside, the head section at this point being greater than the stem section. The section of the stem is of rectangular trapezoid shape. The stem is hollowed at regular distances over its length. The soil comes to be housed in the hollows along the stem subsequent to scraping achieved by rotation of the stem. During rotation, scraping is made by the projecting part formed along the length of the stem by the oblique side of the stem section. The part of the driving head that is offset is located perpendicularly above this projecting part so as to widen the hole and thereby provide some freedom of rotation to the projecting part in the widened part of the hole when the auger is driven down. Once rotation of the stem is initiated, the projecting part is no longer in the widened part of the hole and comes into contact with the earth on the side walls of the hole where the hole is not widened. When this type of auger is driven downwards, the stem undergoes ground friction and it becomes difficult to drive the auger down. This type of auger is made up of several parts and does not comprise any specific means to withstand the shock wave generated when it is driven down using a tool such as a hammer. In addition, this type of auger cannot be used to take samples over the entire depth.

OBJECTS AND SUMMARY OF THE INVENTION

The purpose of the present invention is therefore to overcome the disadvantages of the prior art by making available an auger formed of means to drive down the auger whose shape is able to reduce friction of material on the tool when it is driven down or drawn upwards. In addition the auger of the invention can be used to collect samples of material over the entire depth in a single boring operation.

This objective is achieved by a device to take samples in a material of granular or powdery composition comprising a stem fitted at one end with a wheel intended to rotate the tool and at the other end with a driving head, characterized in that the head is mounted symmetrically on the stem and comprises lower and side parts of streamlined shape, the stem having a shape designed to scrape the material over the entire depth and the head having a cross section that is smaller than, equal to or greater than the cross section of the stem, in proportions determined in relation to the nature and/or moisture content of the material to be sampled.

According to another particularity, the stem comprises at least one longitudinal groove and, as a continuation of one of the inner surfaces of groove, has a part which projects beyond the stem which, along the entire length of the stem, can scrape the soil by rotation of the stem.

According to another particularity, the cross section of the stem is in the shape of a spiral grooved on the inside of the section following the line of junction between the two free ends of the spiral to form a projecting part.

According to another particularity, the cross section of the stem is in the shape of a disc that is grooved on the inside of the section, one of the edges of the disc located either side of the groove being extended outwards to form the projecting part.

According to another particularity, the head section is greater than the section of the main body of the stem, that is without the projecting part, to a maximum proportion of 40%.

According to another particularity, the projecting part can be removed from the stem.

According to another particularity, the projecting part is inclined outwards through a certain angle in the opposite direction to the direction of scraping.

According to another particularity, the stem is hollow and one inner surface of the groove, belonging to this projecting part, is open so as to allow the soil to enter the hollow stem when the auger is rotated.

According to another particularity, the groove is parallel to a radial plane of the stem.

According to another particularity, the cross section of the stem can vary in size along the length of the stem.

According to another particularity, the stem cross section on the upper part of the stem is greater than the cross section of the lower part of the stem so as to collect dry soil on the surface.

According to another particularity, the groove is sufficiently wide to collect the soil scraped during rotation of the stem.

According to another particularity, the stem is graduated from bottom to top to obtain information on the sampling depth of the tool.

According to another particularity, the head is in the shape of an olive symmetrically mounted on the stem along the longer axis of the olive.

According to another particularity, several olive head diameters are available depending upon the nature and/or moisture content of the ground.

According to another particularity, the olive heads are screwed onto the stem.

According to another particularity, a bar that is transversal relative to the stem axis, positioned between the wheel and the head, is used to facilitate driving the tool into the ground.

According to another particularity, at least one handle rises from the wheel to facilitate grasping of the tool when it is rotated.

According to another particularity, a driving means is intended to drive the auger into the ground.

According to another particularity, the device, at its end opposite the driving end, comprises a male tip intended to be coupled co-axially with a female tip of an inertia hammer, a rod sliding within the inertia hammer in the extension of the female tip which strikes the male tip so as to drive the device downwards.

According to another particularity, the wheel is a floating wheel via shock-absorbing parts which deaden the shockwave and the vibrations generated when striking.

The invention with its characteristics and advantages will become clearer on reading the following description which refers to the appended drawings.

BRIEF DESCRIPTION OF THE DRAWINGS

FIG. 1 is a perspective view of an auger according to the invention driven into the ground, FIG. 2 shows the lower part of an auger according to the invention after one rotation of the tool.

DESCRIPTION OF THE PREFERRED EMBODIMENTS

Figure 3:
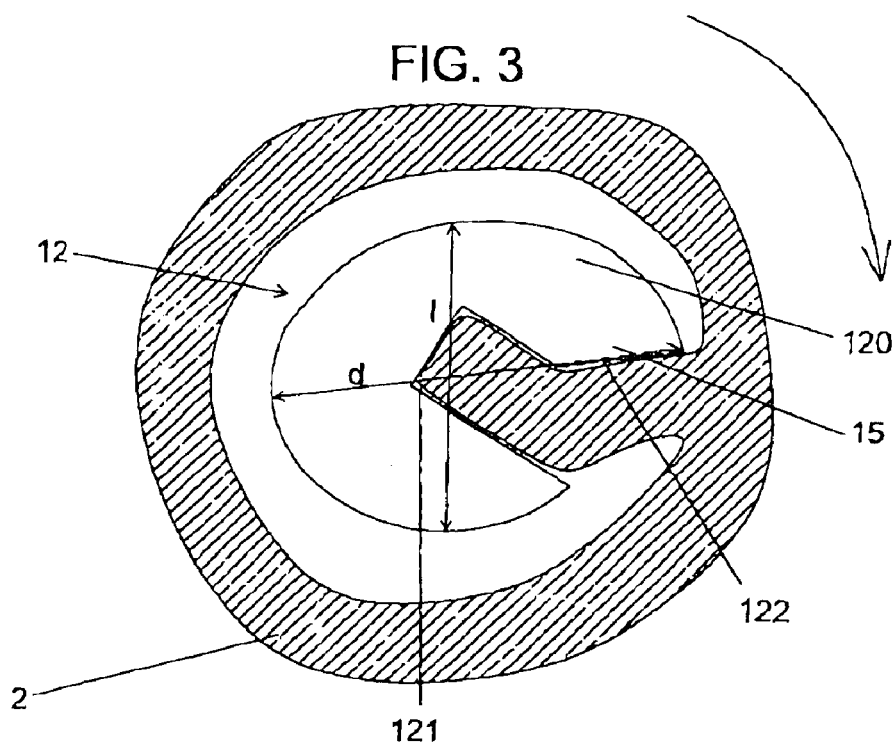
FIG. 3 is an overhead view of the stem driven into the ground.

The invention will be described with reference to FIGS. 1 to 6.

The sampling device or auger 1 according to the invention shown in FIG. 1, is intended to be driven downwards to a certain depth in any type of granular or powdery material, to take samples thereof for analysis. The sampling device of the invention may therefore be driven into organic matter of farm fertilizer type such as manure, litter, droppings, of compost type, solid sludge or in waste. The device of the invention may be driven into fodder such as food stored in silos, corn for example. The device of the invention is also intended to be driven into the ground to a certain depth to take samples of soil, snow, sand for example for their analysis in order to determine the land content of certain substances. If the ground is soil, analysis may involve substances such as nitrates, heavy metals for example or pesticides. Other uses of the device are also possible. The device of the invention may also be used for ground surveys for the statistical determination of average ground depth accessible by roots or any type of groundwork tool, or for calculating different parameters such as groundwater reserves. Similarly, a further use may concern observation of the different layers of the ground for scientific or teaching purposes.

For soil sampling in the ground 2, procedure is as follows. In a field several samples are taken at various sites and at different depths, depending upon the substance it is wished to detect. Nitrates, for example, are detected at a depth of approximately 90 cm which requires land that is sufficiently soft to drive down the auger 1. This is the reason why nitrate analysis of soil is generally conducted between October and March, the time of the year when the soil is wettest and therefore less compact.

The device of the invention or auger 1 is preferably used in moist ground so that it is easier to insert, but it may be used in dry ground 2.

The auger 1 of the invention shown in FIG. 1 is formed of a stem 12, surmounted by a wheel 10 used to drive down or lift up the auger, this wheel 10 comprising a handle 11 to facilitate grasping the wheel 10 when the tool is rotated to take a soil sample. This wheel 10 may, for example, comprise a knob 110 that can freely rotate on the handle 11 of the wheel 10 making it easy to operate the tool when it is rotated. The auger 1 of the invention ends in a streamlined head 13, that is olive-shaped for example, so that the earth can easily slide along the head 13 without sticking to the stem 12 when the auger 1 is driven down or lifted up. The head 13 is therefore streamlined on its lower parts and upper parts, these two parts being delimited by the part of the head 13 having the largest head section. The lower streamlined parts of the head 13 loosen the soil when the auger is driven down into the ground and the upper streamlined parts of the head 13 allow the soil to flow over the head when the auger 1 is lifted back up.

The head 13 may also have a dissymmetrical shape. The olive-shaped head 13 may, for example, be mounted symmetrically on the stem 12 so that the soil can easily slide along the head 13 all around the stem 12 without sticking to the stem 12. The head 13 may for example be screwed onto the stem 12. Other means for fixing the head 13 may be considered such as press-fit or welding means. A cross bar 14 fixed to the stem 12 facilitates initial penetration of the auger 1 into the dryer layer of the ground by providing a fulcrum for the feet or knees. This bar 14 is placed symmetrically for example on the stem 12 at a height of a little over 90 cm.

The stem 12 is intended to collect a soil sample over the entire depth to which the auger 1 is driven, 90 cm for example. Therefore, the user obtains a global sample and it is not necessary to take several samples at different depths in the same place. For this purpose, the stem 12 of the invention comprises a cross section 120 specifically shaped to take a soil sample. This soil sample may for example be taken by scraping the earth. The section 120 of stem 12 may for example be in the shape of a flattened spiral so that it can easily be rotated when the user takes the sample. A groove, for example, in the shape of a channel 121 is made towards the inside of the section following the junction line of the two free ends of the spiral section. The projecting part, formed on the whole length of the stem 12 by the spiral section, scrapes the soil bored by the head 13 which comes to house itself in the channel 121. This projecting part therefore forms a scraper lip 15 which samples the soil along the entire length of the stem 12. The scraper lip 15 may for example, as shown in FIG. 3, be inclined outwards by a certain angle, in the opposite direction to the direction of scraping indicated by the curved arrow in FIG. 3. The stem 12 is graduated over its entire length from bottom to top so as to visualize the depth of penetration of the tool and to take the sample on the length of the stem 12 at the desired depth once the auger 1 is lifted back up.

The maximum section of the head 13 is smaller than, equal to, or greater than the section of the stem 12. The size of the head 13 varies in relation to the type of land or material in which the auger 1 of the invention is to be used.

If the section of the head 13 is smaller than the section of the stem 12, only the end of the scraper lip 15 of the stem 12 projects in relation to the head 13. This projection is a few millimeters, no more than 5 mm, and preferably 3 mm. This projection does not hinder the penetration into or lifting back of the auger 1 from the ground, since only a small surface is exposed and likely to be subjected to ground friction when the auger 1 is lowered or lifted.

The head 13 may also have a maximum section that is greater than the section of the stem 12. In this case, the scraper lip does not project beyond the maximum section of the head 13 and is therefore fully protected by the head 13 when the auger of the invention 1 is lowered or lifted. This section must be no more than 40% greater than the section of the main body of the stem 12, that is to say without the scraper lip 15. In this case, the end of the scraper lip (15) may for example project by 0.5 mm relative to the maximum section of the head 13. The section of the head 13 is preferably 0 to 30% greater than the section of the main body of the stem 12.

A head section that is equal to or greater than the section of the stem 12 may be considered when the ground 2 is wet for example. If the ground is wet, when the auger 1 is being driven or is fully driven down, the earth loosens and flattens against the stem 12. The soil pushed towards the stem 12 can then be scraped by the scraper lip 15 which nonetheless does not project beyond the head 13. At all events, the head 13 is streamlined and facilitates the sinking and lifting of the auger 1 avoiding ground friction along the length of the stem 12 when the auger 1 is lowered or lifted.

The formed scraper lip 15 may be more marked on the upper part than on the lower part of the stem 12. In general, soil is dryer on the surface and therefore tends to loosen less, being pushed to a lesser extent against the stem 12; a larger radius of scraping action is therefore required to take a soil sample.

The device operates in the following manner. For the analysis of various substances, including nitrates in wet ground 2, the auger 1 is driven down to a depth of 90 cm, as visualized on the graduations of the stem 12, via the olive-shaped head 13 by exerting pressure on the wheel 10 with the hand and chest and on the intermediate cross bar 14 with the feet. Since the head 13 is streamlined, the soil slides along the head 13 when the auger 1 is driven down but does not stick to the stem 12 since the soil is wet. On reaching the desired depth, the user causes the auger 1 to rotate using the wheel 10, the handle 11 and the free knob 110; the soil is then scraped by the scraper lip 15 of stem 12 and comes to be housed in channel 121. The user lifts back the auger 1 and obtains a complete profile of the land over a depth of 90 cm. Samples or cores can then be taken at different depths, for example every 15 cm, using the graduations on the stem 12.

Several diameters D of the olive-shaped head 13 may be used depending upon the nature of the land. In Summer when the land is dry, the earth does not loosen towards the bore centre, and a head 13 with a slightly smaller cross section than the stem section must be used so that the scraper lip 15 projects beyond the head 13 and is able to scrape the dry soil. According to the invention, the available head sizes range from 18 to 27 mm in diameter D. The diameter D of the olive is chosen in relation to the nature and/or moisture content of the material in which the auger 1 is driven and in relation to the section 1 of stem 12. The section of the main body of the stem 12, that is to say without the scraper lip 15, defined as 1 in FIG. 3, may be 15 to 18 mm for example. The diameter of the cross section 120 of stem 12, defined as d in FIG. 3, is no more than approximately 27 mm at the end of the scraper lip. This diameter d may also vary along the length of the stem 12. Indeed, the stem's scraper lip 15 may be more marked on its upper part so as to sample the dry soil on the surface which does not loosen towards the stem 12 after the auger of the invention 1 has been driven into the ground.

Figure 4:
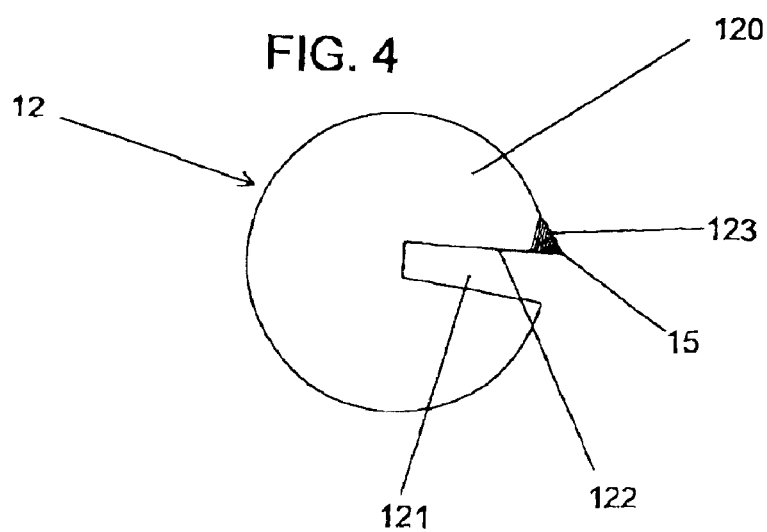
FIG. 4 shows a variant of embodiment of the stem cross section.

According to another variant of embodiment shown in FIG. 4, the cross section of stem 12 is in the shape of a grooved disk which, over the entire length of stem 12, forms the channel 121 to collect the soil. One of the edges 123 located either side of channel 121 is elongated so as to form the scraper lip intended to scrape the soil when the auger 1 is rotated. Channel 121 is hollowed so that it is preferably offset and parallel to a radial plane of the stem 12.

According to one variant, the scraper lip 15 of the invention can be removed from the stem 12. The stem 12 may for example have a section in the shape of a disc as shown in FIG. 4. The channel 121 is hollowed over the entire length of the stem 12. The scraper lip 15 may adapt to the stem in the vicinity of channel 121. The scraper lip 15 may for example be fixed to the stem 12 by press-fit means in line with one of the outer edges of channel 121.

According to one variant, the scraper lip 15 may for example be articulated to form a hinge with stem 12 over the entire length of the stem 12.

According to one variant, the scraper lip 15 may be a sharp, plane blade or may be indented at its scraper end, the indents optionally being more or less distanced and projecting to a greater or lesser extent. These different variants in the configuration of the scraper lip depend upon the type of material to be sampled.

According to one variant, for example when the ground is very soft, the sampling channel 121 may be shuttered along its entire length to prevent the channel 121 from being filled when the auger is driven downwards, so as not to pollute the sample to be taken. This shuttering means may be formed of a rod whose shape is complementary to the shape of the channel 121 and slides within channel 121. This rod, once the auger has been driven downwards, may be withdrawn by the user before taking the sample by rotating stem 12 of auger 1.

According to another variant of embodiment, the stem 12 is hollow and the inner surface 122 of channel 121 adjacent to the scraper lip 15 is open so as to allow the soil to enter when the auger is rotated. After rotation of the auger 1, the soil comes to be housed inside stem 12. By unscrewing the head 13 for example it may be possible to collect the core of soil formed inside the stem 12 after the auger 1 is lifted back.

According to another variant of embodiment, the auger 1 of the invention is adapted to a driving means, such as a jack for example or a lever arm. The driving means is intended to drive down the auger 1 into the ground by applying pressure on the upper part of the auger 1. According to this variant, means are intended to maintain the auger 1 substantially perpendicular to the ground when it is driven down by the driving means.

According to the invention, in soil that is sufficiently moist, the auger 1 is generally driven into the ground by hand. However, in some situations, it may be necessary to have recourse to a specific inertia hammer 16. This is the case for example when the soil 2 is close packed or its surface is frozen, when the soil is compacted, when the soil 2 is humid but with a high clay or stone content.

Figure 5:
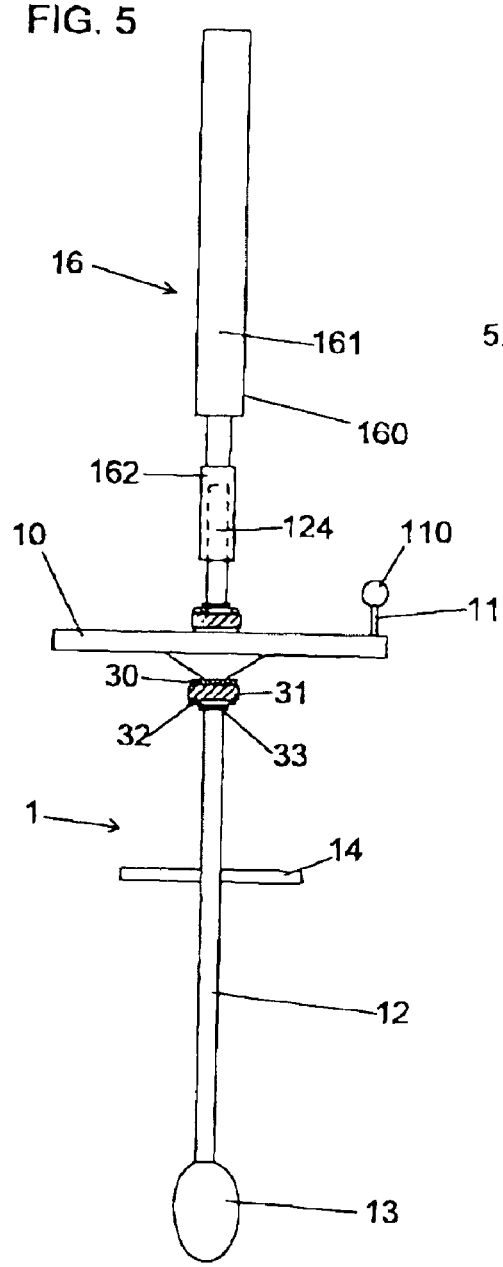
FIG. 5 shows the auger of the invention and the inertia hammer.
Figure 6:
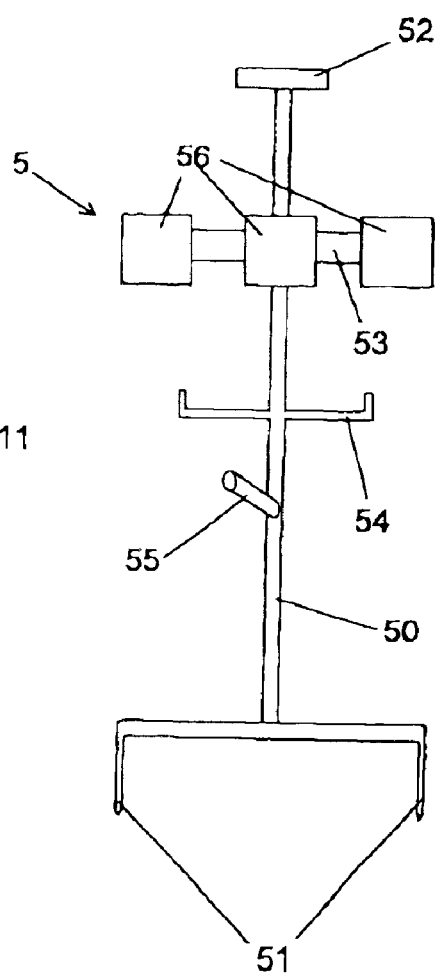
FIG. 6 shows a "carry-all" device.

The stem 12 of the auger 1 is extended at the end opposite the driving end of the auger 1 to form a male end part 124 as shown in FIG. 5. The male end part 124 comprises a tempered head to resist striking by the hammer. The inertia hammer 16 is formed of a tube 160 comprising a handle 161. In this tube 160 a sliding rod is inserted of which one end is intended to strike the male end part of the auger 1. One end of the inertia hammer 16 comprises a female end part 162 intended to be coupled with the male end part 124 formed on auger 1. A part in Teflon is inserted in the head of the hammer to prevent repercussions of the shockwave when the hammer strikes the auger 1 to drive it downwards.

The auger 1 also comprises a floating handle which dampens the shock wave and the vibrations generated by the striking, using an inertia hammer for example. The stem 12 is for example mounted on wheel 10 via an assembly part. Between the stem and the wheel a gasket 30 bearing upon the wheel 10 is positioned, underneath which there is a shock absorbing part formed of a rubber 31 under which is another gasket 32 tightened against the rubber 31 by means of a pin 33. This system is reproduced above the wheel 10 between the male end part 124 and the wheel 10.

Various accessories may be used when taking a sample. For example a "carry-all" device shown in FIG. 6 can be used to hold the tools and accessories needed to take a sample. This device 5 is formed of a stem 50 at one end of which are two parallel tips 51 which can be driven into the ground near at hand for the user of the auger of the invention. At the other end of stem 50, device 5 comprises a handle 52 for carrying the device and driving it into the ground. The device may for example comprise three cross bars 53, 54, 55. One first cross bar 53, an upper bar for example, is intended to carry the plastic bags 56 in which the soil samples are to be placed. The second cross bar 54 is intended to carry accessories such as a brush, knife or scraper. The scraper can be used in particular to scrape out the soil housed in the channel after lifting the auger 1 out of the ground. A final cross bar 55 can be used for example as an auger rest.

It must be obvious for persons skilled in the art that the present invention enables embodiments under numerous other specific forms while remaining within the scope of application of the invention as claimed. Therefore, the embodiments described must be considered as illustrative examples which may be modified within the domain defined by the scope of the appended claims, and the invention is not to be limited to the details given above.

What is claimed is:

1. A device for taking samples in a material of granular or powdery composition comprising:
    a stem,
    means mounted at one end of said stem for rotating the device,
    a driving head at an opposite end of said stem and mounted symmetrically on the stem, said head including lower and side parts of streamlined shape, the stem being of a predetermined shape and comprising at least one longitudinal groove having inner surfaces, an extension of one of the groove's inner surfaces having a part projecting laterally beyond the stem and over the entire length of the stem for scraping material to be sampled by rotation of the stem and directing the material to be sampled into the groove, said head having a maximum cross section in proportions determined with the cross section of the stem in relation to the nature or moisture content of the material to be sampled.

2. A device according to claim 1 wherein the stem has a cross section having the shape of a spiral grooved towards the inside of a section following a line of a junction between two free ends of the spiral and thereby forming a projecting part.

3. A device according to claim 1 wherein the stem has a cross section having the shape of a disc grooved towards an inner part of a section on one side of the groove and extending laterally outwardly of said stem to form said projecting part.

4. A device according to claim 1 wherein the head has a maximum cross section no more than 40% greater than the cross section of the stem without said projecting part.

5. A device according to claim 1 wherein said projecting part is removable from the stem.

6. A device according to claim 1 wherein said projecting part is inclined laterally outwardly through a predetermined angle in an opposite direction to the direction of scraping.

7. A device according to claim 1 wherein the stem is hollow, said one inner surface of the groove being open to enable soil to enter the hollow stem upon rotation of the stem.

8. A device according to claim 1 wherein the groove is parallel to a radial plane of the stem.

9. A device according to claim 1 wherein the cross section of the stem varies along the length of the stem.

10. A device according to claim 9 wherein the cross section of the stem on the upper part of the stem is greater than the cross section on the lower part of the stem enabling the sampling of dry soil on the surface.

11. A device according to claim 1 wherein the groove is sufficiently wide to collect the soil scraped during rotation of the stem.

12. A device according to claim 1 wherein the stem is graduated from bottom to top to obtain information on the sampling depth of the tool.

13. A device according to claim 1 wherein the head is olive shaped and is symmetrically mounted on the stem about a long axis of the olive-shaped head.

14. A device according to claim 13 including a plurality of said olive-shaped heads having different diameters for use depending upon the nature or moisture content of the ground.

15. A device according to claim 13 wherein the olive-shaped heads are threadable onto the stem.

16. A device according to claim 1 including a bar placed crosswise relative to the axis of the stem and positioned between the means for rotating the device and the head to facilitate entry of the tool into the ground.

17. A device according to claim 1 wherein the means for rotating the device includes at least one handle to facilitate grasping the device when rotated.

18. A device according to claim 17 wherein said one end of the device has a male projection, and inertial hammer including a female end coaxially coupled to said male end and a rod slidable inside the female end for striking the male end to drive the device into the ground.

19. A device according to claim 18 wherein the means for rotating the device includes a shock absorber for dampening the shockwave of vibrations generated by said inertial hammer.

20. A device according to claim 1 including a driving means for driving the device into the ground.

* * * * *